United States Patent
Taniguchi et al.

(10) Patent No.: US 8,587,310 B2
(45) Date of Patent: Nov. 19, 2013

(54) MAGNETIC RESONANCE IMAGING DEVICE

(75) Inventors: Yo Taniguchi, Kokubunji (JP);
Yoshitaka Bito, Kokubunji (JP); Shoichi Miyawaki, Kashiwa (JP); Hiroyuki Takeuchi, Kashiwa (JP); Suguru Yokosawa, Kokubunji (JP)

(73) Assignee: Hitachi Medical Corporation, Tokyo (JP)

(*) Notice: Subject to any disclaimer, the term of this patent is extended or adjusted under 35 U.S.C. 154(b) by 405 days.

(21) Appl. No.: 13/054,155
(22) PCT Filed: Jul. 22, 2009
(86) PCT No.: PCT/JP2009/063108
§ 371 (c)(1),
(2), (4) Date: Jan. 14, 2011

(87) PCT Pub. No.: WO2010/035569
PCT Pub. Date: Apr. 1, 2010

(65) Prior Publication Data
US 2011/0112393 A1    May 12, 2011

(30) Foreign Application Priority Data
Sep. 25, 2008 (JP) .................. 2008-245626

(51) Int. Cl.
*G01V 3/00* (2006.01)
(52) U.S. Cl.
USPC ........................ 324/309; 324/307
(58) Field of Classification Search
USPC .......... 324/309, 307, 310, 312, 314; 382/128
See application file for complete search history.

(56) References Cited

U.S. PATENT DOCUMENTS

| | | | | |
|---|---|---|---|---|
| 6,239,599 B1* | 5/2001 | Zhou et al. | ..................... | 324/309 |
| 6,323,646 B1* | 11/2001 | Zhou et al. | ..................... | 324/309 |
| 7,205,763 B2* | 4/2007 | Porter | ..................... | 324/306 |
| 7,689,015 B2* | 3/2010 | Takai | ..................... | 382/128 |
| 8,040,133 B2* | 10/2011 | Pfeuffer et al. | ............... | 324/309 |
| 8,283,925 B2* | 10/2012 | Auslender et al. | ............ | 324/309 |
| 2012/0271584 A1* | 10/2012 | Xu et al. | ..................... | 702/106 |

FOREIGN PATENT DOCUMENTS

| | | |
|---|---|---|
| JP | 09-276243 | 10/1997 |
| JP | 2006-262928 | 10/2006 |
| JP | 2009-160051 | 7/2009 |

OTHER PUBLICATIONS

Nikolaos G. Papadakis et al., Gradient Preemphasis Calibration in Diffusion-Weighted Echo-Planar Imaging, Magnetic Resonance in Medicine 44:616-624 (2000).

T. Smponias et al., K-space Correction of Eddy Current-Induced Distortions in DW EPI, Proc. Intl. Soc. Mag. Reson. Med. 11 (2004).

* cited by examiner

*Primary Examiner* — Louis Arana
(74) *Attorney, Agent, or Firm* — Antonelli, Terry, Stout & Kraus, LLP.

(57) ABSTRACT

In the diffusion-weighted imaging, amounts of distortion and amounts of phase offset of k-space data due to a temporally changing magnetic field error induced by eddy currents and vibrations associated with application of a diffusion-weighted gradient magnetic field pulse are corrected with good precision to improve image quality. Characteristic data for correcting distortion of k-space data are calculated for every position in the slice direction as peak shifts of projections observed between the cases of applying and not applying an MPG pulse. As the characteristic data, amounts of distortion in the read-out direction and the phase encoding direction and phase offset amounts in a slice plane are calculated.

13 Claims, 9 Drawing Sheets

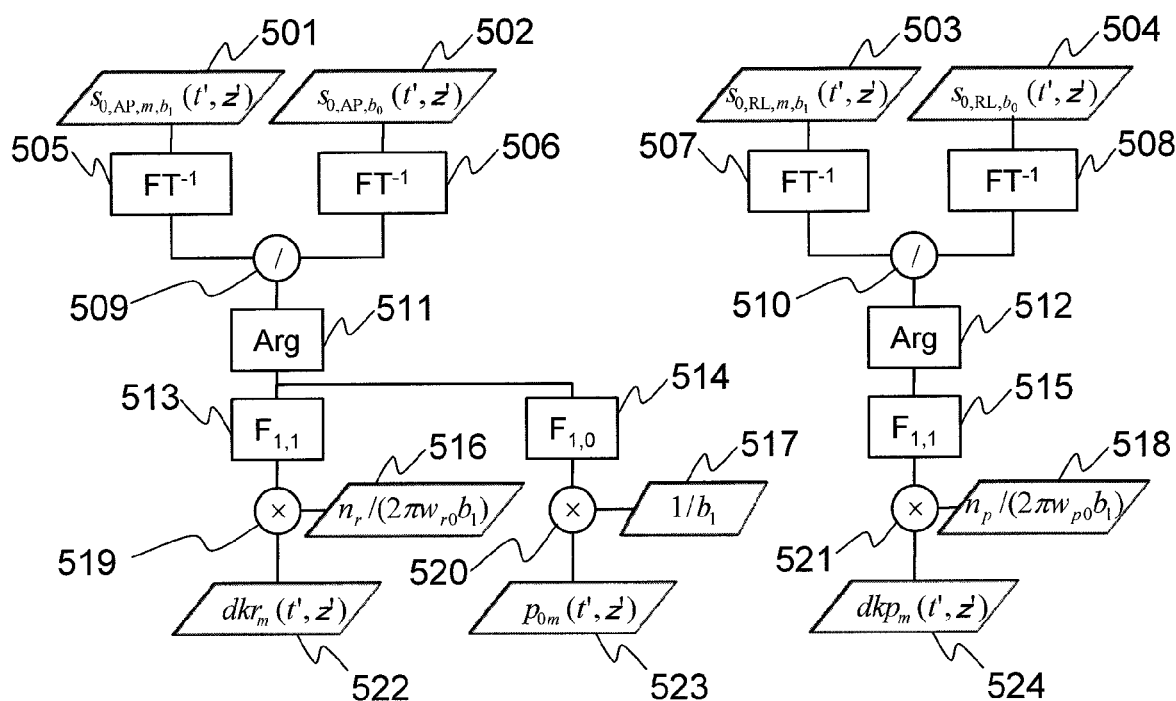

Fig. 9A
Fig. 9B
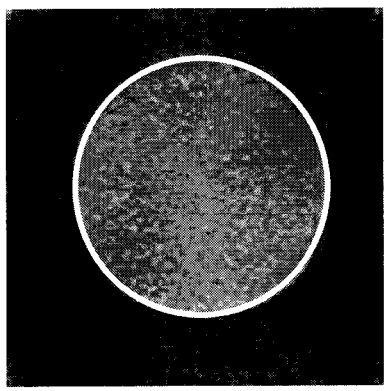
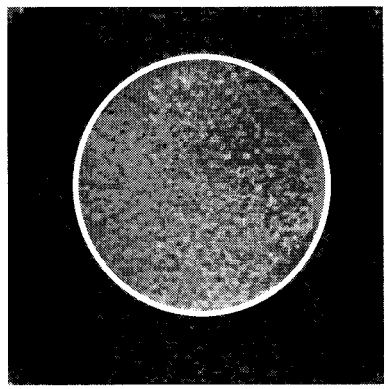
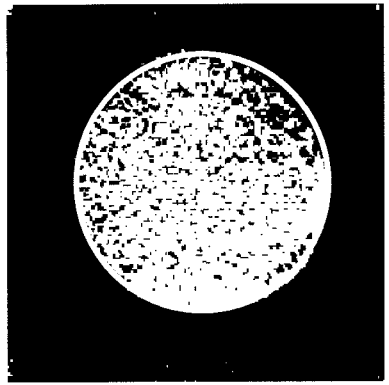
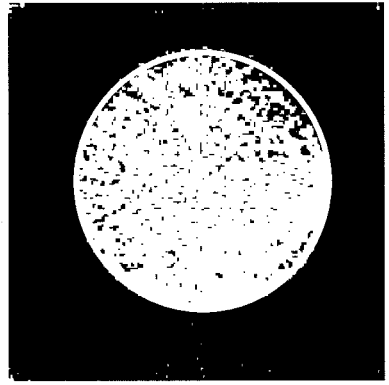

ically changing magnetic field error generated by eddy currents and vibrations associated with application of a diffusion-weighted gradient magnetic field pulse with good precision, and thereby improving image quality in the diffusion-weighted imaging.

MAGNETIC RESONANCE IMAGING DEVICE

TECHNICAL FIELD

The present invention relates to a magnetic resonance imaging technique. In particular, the present invention relates to a technique for correcting influences of fluctuation of magnetic field originating in eddy current and vibration in diffusion-weighted imaging.

BACKGROUND ART

A magnetic resonance imaging (MRI) device is a medical diagnostic imaging device, which applies a radio frequency magnetic field and a gradient magnetic field to a subject placed in a static magnetic field, detects signals generated by nuclear magnetic resonance in the subject, and forms an image from the signals.

As a method capable of obtaining images in which cerebral infarction at an acute stage, tumors etc. are emphasized with high signal strength, there is the diffusion-weighted imaging in which imaging is performed with emphasizing diffusion of water molecules. Since cerebral infarction at an acute stage is in a state of cellular edema, such diffusion is suppressed. Further, such diffusion is also suppressed in tumors densely containing cells. Therefore, in the diffusion-weighted imaging, diffusion coefficients of these sites become smaller than those of other tissues, and signals from them are detected with higher strengths.

As a typical imaging technique for obtaining diffusion-weighted images, there is the diffusion-weighted echo planar imaging. This method is an ultra high-speed imaging technique based on the single shot echo planar imaging, additionally using an MPG (motion probing gradient, diffusion-weighted gradient magnetic field) pulse, which is a gradient magnetic field pulse for emphasizing the diffusion. Since the MPG pulse generally has a higher strength and is applied for a relatively longer time, eddy currents and vibrations thereby induced result in fluctuation of magnetic field, which eventually degrades image quality.

There is a technique for suppressing influence of eddy currents by measuring eddy currents generated upon applying MPG as gradient magnetic field components of the slice direction, and applying a gradient magnetic field so as to cancel the components at the time of main scan (refer to, for example, Non-patent document 1).

In that technique, signals are measured by using a pulse sequence for the diffusion-weighted echo planar imaging with read-out gradient magnetic field pulse strength and phase-encoding gradient magnetic field strength of zero. This measurement is performed for positions of a plurality of slices in a predetermined slice direction, and temporal change of the magnetic field induced by MPG is measured for each slice position. Then, the change of the magnetic field is fitted with a linear function to obtain temporal change of the static magnetic field and temporal change of the gradient magnetic field in the slice direction. The absolute term of the obtained linear function represents the static magnetic field component generated by MPG, and the first order term represents the gradient magnetic field component in the slice direction. At the time of the diffusion-weighted imaging, a static magnetic field and a gradient magnetic field of the slice direction are applied so as to cancel those static magnetic field component and gradient magnetic field component, and thereby suppress the eddy currents generated by MPG.

Moreover, there is also a method for suppressing artifacts by a post-processing using temporal change of the magnetic field induced due to eddy currents generated by MPG, which is obtained by the aforementioned technique, not applying a gradient magnetic field for canceling them at the time of imaging (refer to, for example, Non-patent document 2). In this technique, phase shift (phase offset) and distortion of k-space data are calculated from the static magnetic field components and the gradient magnetic field components measured as described above, and images are corrected by phase offset correction and gridding to eliminate the influences of the eddy currents induced by MPG.

PRIOR ART REFERENCES

Non-patent Documents

Non-patent document 1: Papadakis N. G., Gradient Preemphasis Calibration in Diffusion-Weighted Echo-Planar Imaging, Magn. Reson. in Med., 2000, 44:616-624

Non-patent document 2: Smponias T., k-space Correction of Eddy Current-Induced Distortions in DW EPI, Proc. Intl. Soc. Mag. Reson. Med., 2004, 11:2187

SUMMARY OF THE INVENTION

Problem to be solved by the Invention

In the above-mentioned method, since the strengths of the read-out gradient magnetic field pulse and the phase encoding gradient magnetic field pulse are zero at the time of measuring the eddy current, fluctuation of magnetic field distributed in the slice plane is integrated and therefore cannot be measured. For example, when the slice direction at the time of the measurement of eddy current is the x-direction, fluctuation of magnetic field in the y-direction or z-direction cannot be measured. Therefore, the obtained correction value for the gradient magnetic field component of the x-direction is a constant not depending on the change in the y- or z-direction. Accordingly, when a diffusion-weighted imaging in which a slice direction is the z-direction is performed, for example, the same correction value is used for the correcting an eddy current of the x-direction in a slice regardless of the slice position z. However, in general, eddy currents are not spatially uniform, and therefore the optimal correction value should differ depending on the slice position z. Therefore, by the aforementioned method, an appropriate correction value cannot be obtained, and correction cannot be attained with good precision.

The present invention has been accomplished in light of the above-mentioned circumstances, and provides a technique for correcting distortion of k-space data due to temporally changing magnetic field error generated by eddy currents and vibrations associated with application of a diffusion-weighted gradient magnetic field pulse with good precision, and thereby improving image quality in the diffusion-weighted imaging.

Means to Solve the Problem

According to the present invention, characteristic data for correcting distortion of k-space data are calculated for every position in a slice direction on the basis of peak shifts between echoes obtained with and without applying an MPG pulse. As the characteristic data, distortion amount and phase offset are calculated for the read-out direction and phase encoding direction in the slice plane, respectively. Then, the data in the k-space are corrected by using the calculated characteristic data at the time of image reconstruction.

Specifically, the present invention provides a magnetic resonance imaging device comprising an imaging means for applying a radio frequency magnetic field and a gradient magnetic field to a subject placed in a static magnetic field and detecting magnetic resonance signals generated from the subject, a calculation means for processing the magnetic resonance signals detected by the imaging means, and a control means for controlling the imaging means and the calculation means, wherein the imaging means comprises a diffusion-weighted imaging execution means for detecting the magnetic resonance signals according to a pulse sequence including a diffusion-weighted gradient magnetic field pulse, and a reference data acquisition means for obtaining reference data for detecting distortion amounts of k-space data caused by the diffusion-weighted gradient magnetic field pulse at an arbitrary position in a slice direction, and the calculation means comprises a characteristic data calculation means for calculating distortion amounts for a read-out direction and a phase encoding direction and phase offset amounts at an arbitrary position in the slice direction from the reference data as characteristic data of the amounts of distortion of k-space data, a correction means for correcting the k-space data constituted by the magnetic resonance signals acquired by the diffusion-weighted imaging execution means by using the characteristic data, and an image reconstruction means for reconstructing an image from the data corrected by the correction means.

Effect of the Invention

According to the present invention, in the diffusion-weighted imaging, distortion of k-space data due to a temporally changing magnetic field error induced by eddy currents and vibrations associated with application of a diffusion-weighted gradient magnetic field pulse can be corrected with good precision, and thus image quality is improved.

BRIEF DESCRIPTION OF THE DRAWINGS

FIG. 5A is a drawing for explaining the characteristic data calculation processing for AP according to an embodiment of the present invention.

FIG. 5B is a drawing for explaining the characteristic data calculation processing for RL according to an embodiment of the present invention.

FIG. 9A are drawings for explaining effect of correction according to an embodiment of the present invention (results of correction according to a conventional method).

FIG. 9B are drawings for explaining effect of correction according to an embodiment of the present invention (results of correction according to the technique of the embodiment).

MODES FOR CARRYING OUT THE INVENTION

<<First Embodiment>>

The first embodiment of the present invention will be explained below. Hereafter, in all the drawings for explaining embodiments of the present invention, elements having the same function are indicated with the same symbols, and repetition of explanation thereof is omitted.

Figure 1:
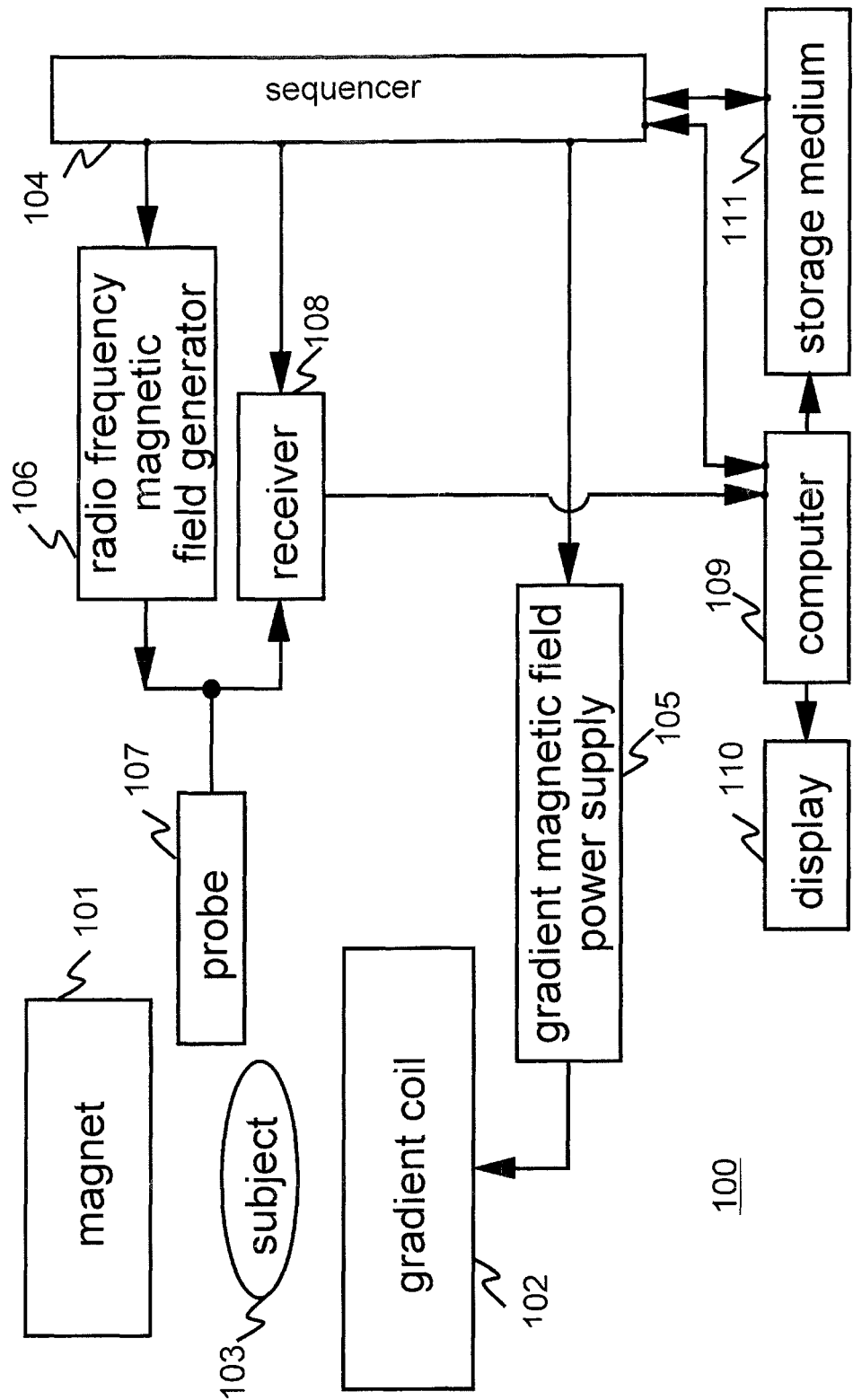
FIG. 1 is a block diagram showing schematic configuration of an MRI device according to an embodiment of the present invention.

First, an MRI device of this embodiment will be explained. FIG. 1 is a block diagram showing a schematic configuration of an MRI device 100 of this embodiment. The MRI device 100 is provided with a magnet 101 for generating a static magnetic field, a gradient coil 102 for generating a gradient magnetic field, a sequencer 104, a gradient magnetic field power supply 105, a radio frequency magnetic field generator 106, a probe 107 for irradiating a radio frequency magnetic field and detecting magnetic resonance signals, a receiver 108, a computer 109, a display 110, and a storage medium 111. A subject (for example, living body) 103 is placed on a bed (patient table) in a space applied with a static magnetic field generated by the magnet 101. The sequencer 104 sends commands to the gradient magnetic field power supply 105 and the radio frequency magnetic field generator 106 to make them generate a gradient magnetic field and a radio frequency magnetic field, respectively. The radio frequency magnetic field is applied to the subject 103 via the probe 107. The magnetic resonance signals generated from the subject 103 are received by the probe 107, and detection is performed by the receiver 108. The nuclear magnetic resonance frequency (detection reference frequency f0) serving as the basis of the detection is set by the sequencer 104. The detected signals are sent to the computer 109, in which signal processing such as image reconstruction is performed. The result of the processing is displayed on the display 110. The detected signals and the measurement conditions may be stored in the storage medium 111, as required.

In the MRI device 100 of this embodiment, as the gradient magnetic field including a diffusion-weighted gradient magnetic field pulse, gradient magnetic fields Gx, Gy and Gz in the three directions along the x, y and z-axes are generated by driving the gradient coil 102 wound in the three directions along the x, y and z-axes with the gradient magnetic field power supply 105 according to a command sent from the sequencer 104 explained later, and applied. More specifically, a slice gradient magnetic field pulse (Gs) is applied in any one of the x, y and z-directions to set a slicing plane (position) in the subject 103, and a phase encoding gradient magnetic field pulse (Gp) and a read-out gradient magnetic field pulse (Gr) are applied in the remaining two directions to encode positional information for respective directions in the magnetic resonance signals.

The sequencer 104 usually controls those components of MRI device 100 so that the components can operate according to timings and strengths programmed beforehand. In particular, among programs, a program describing the radio frequency magnetic field, the gradient magnetic field, and timings and strengths of the signal reception is called pulse sequence. The MRI device 100 of this embodiment obtains diffusion-weighted images. For this purpose, a pulse sequence for DWEPI (Diffusion Weighted Echo Planar Imaging) including a MPG pulse is provided as the pulse sequence.

Further, the computer 109 used in this embodiment is provided with a diffusion-weighted measurement part for directing the sequencer 104 to measure magnetic resonance signals (echoes) according to a DWEPI sequence, and arranging the measured echoes in the k-space, an image reconstruction part for reconstructing an image from the echoes arranged in the k-space, and a correction processing part for performing correction for eliminating influences of magnetic field fluctuation (henceforth referred to as magnetic field error) due to eddy currents and vibrations induced by the MPG pulse from the echoes arranged in the k-space. It is further provided with a reference data acquisition part for performing measurement for obtaining reference data used as the basis for calculating characteristic data used for the correction (reference measurement) via the sequencer 104 in advance of main scan, and a characteristic data calculation part for calculating characteristic data used by the aforementioned correction processing part for the correction from the reference data obtained by the reference data acquisition part. These functions are realized by CPU of the computer 109 by loading programs stored in the storage medium 111 into a memory and executing them.

Figure 2A:
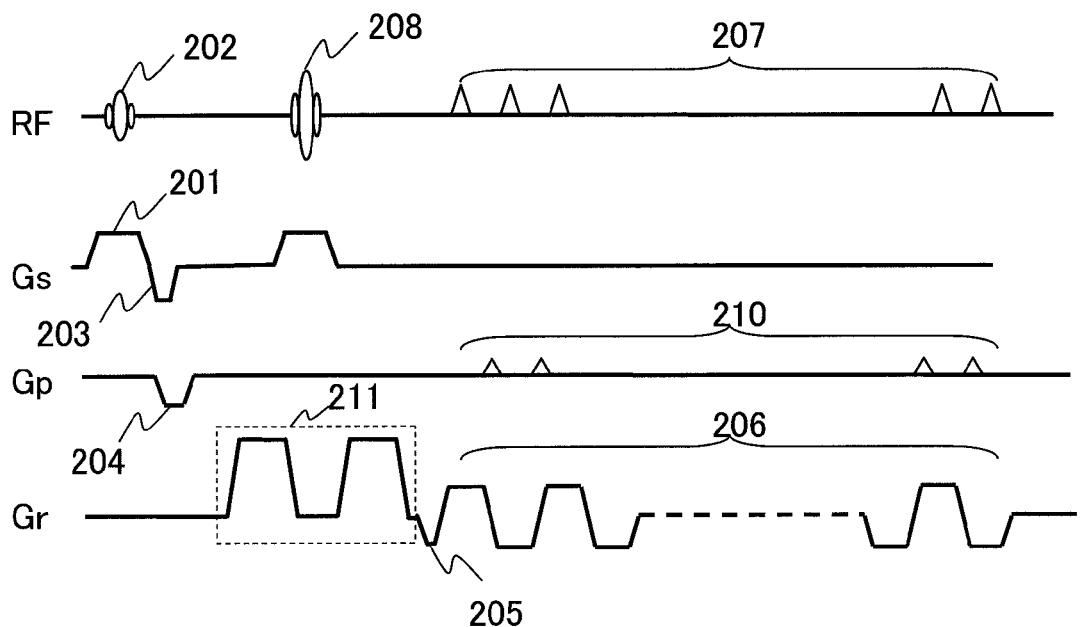
FIG. 2A shows DWEPI sequences with a standard MPG pulse used in an embodiment of the present invention.
Figure 2B:
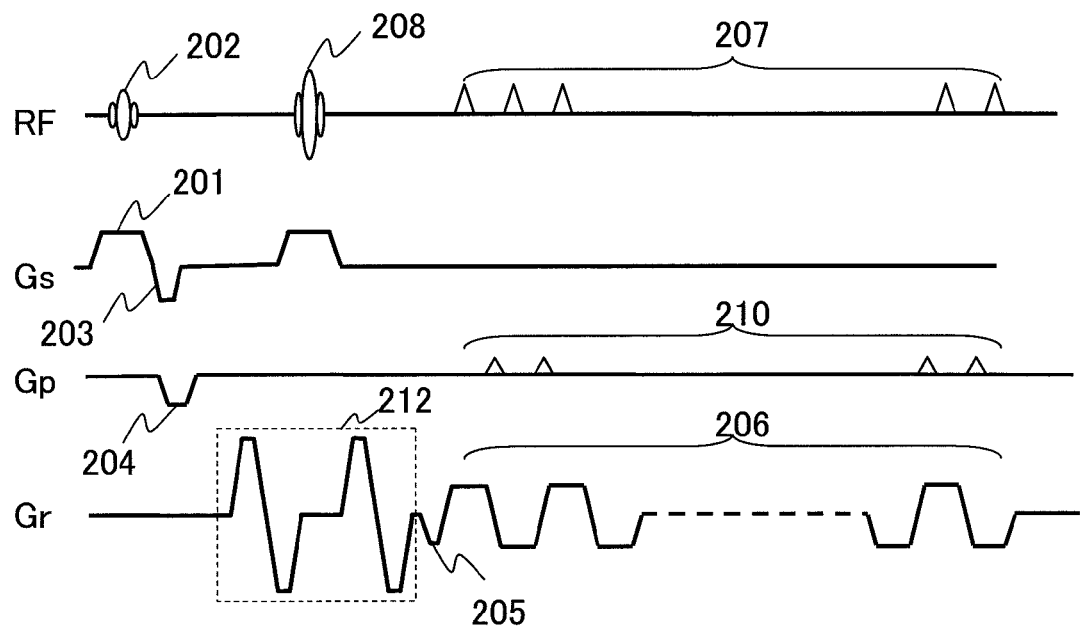
FIG. 2B shows DWEPI sequences with a bipolar type of MPG pulse used in an embodiment of the present invention.

First, there will be explained pulse sequences for realizing the DWEPI method (hereafter referred to as DWEPI sequence) used in the MRI device 100 of this embodiment when diffusion-weighted imaging (main scan) is performed by the diffusion-weighted measurement part. FIG. 2A and FIG. 2B show DWEPI sequences. In these drawings, RF, Gs, Gp and Gr represent axes of the radio frequency magnetic field, slice gradient magnetic field, phase encoding gradient magnetic field, and read-out gradient magnetic field, respectively. In the following explanation of this embodiment, explanations will be made with reference to an example where the slice direction in which the slice gradient magnetic field pulse Gs is applied to determine slice positions is the z-direction, the read-out direction in which the read-out gradient magnetic field pulse Gr is applied is the x-direction, and the phase encoding direction in which the phase encoding gradient magnetic field pulse Gp is applied is the y-direction.

As shown in FIG. 2A and FIG. 2B, in DWEPI, a radio frequency magnetic field (RF) pulse 202 at the resonance frequency fh of proton is irradiated first with application of a slice direction gradient magnetic field pulse 201 in the z-direction to excite protons in a predetermined slice of a subject. And after a slice rephase gradient magnetic field pulse 203 and a phase encoding gradient magnetic field pulse 204 for dephasing for adding positional information in the phase encoding direction (y-direction) to the magnetizations are applied, a 180° pulse 208 is irradiated, and with applying a read-out gradient magnetic field 205 for dephasing and an alternately positive and negative read-out gradient magnetic field pulse 206 for adding positional information in the read-out direction (x-direction), a plurality of magnetic resonance signals (echoes) 207 are measured. During the measurement, in order to add positional information in the phase encoding direction (y-direction), a blip gradient magnetic field 210 is applied whenever the echo 207 is measured.

The MPG pulses 211 and 212 are applied before and after the 180° pulse 208. The following explanations will be made for an example where the MPG pulse is applied in the read-out direction (x-direction). The MPG pulse may be applied in any of the slice direction, the read-out direction, and the phase encoding direction. In order to attain sufficient diffusion weighting, it is necessary to apply an intense MPG pulse for a long application time. Therefore, when diffusion-weighted imaging is performed, eddy currents generated by the MPG pulse and vibrations associated with the application of the MPG pulse cannot be ignored. As for the form of the MPG pulse, there are a standard MPG pulse 211 applied in only one of the positive and negative directions shown in FIG. 2A, and a bipolar type of MPG pulse 212 shown in FIG. 2B, and either one of them may be used. Since the MPG pulse of bipolar type 212 is provided with a pair of positive and negative pulses, it can more suppress the generation of eddy currents compared with the standard MPG pulse 211, but complete suppression cannot be expected. Since the correction for the influence of eddy current is performed by using results of actual measurement in this embodiment, it does not depends on the form of the MPG pulse. Therefore, the MPG pulse used for the DWEPI sequence may have a form of either the MPG pulse 211 or the MPG pulse 212. Hereafter, this embodiment will be explained with reference to an example using the MPG pulse 211.

Figure 3A:
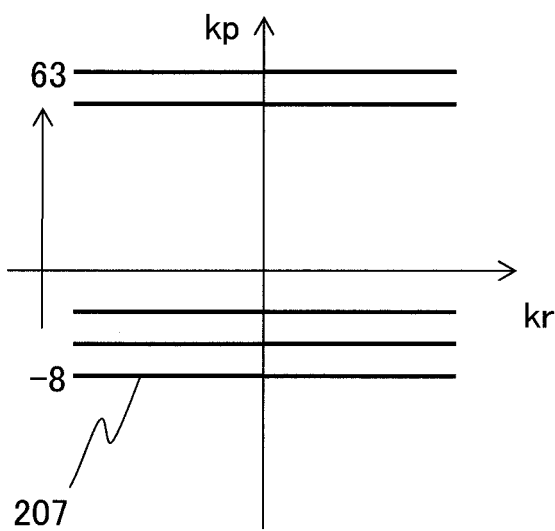
FIG. 3A is a drawing for explaining the k-space according to a general echo planar imaging used in an embodiment of the present invention.

Echoes obtained in the echo planar imaging are generally arranged in the k-space along the read-out direction (kr) as shown in FIG. 3A. This drawing shows an example where the phase encoding amounts of the echoes are −8 to 63 (number of echoes is 72), and the number of the sampling points in the read-out direction is 128. Since the echo planar imaging method is used in this example, the number of echoes in the phase encoding direction (kp) is suppressed. The image reconstruction part reconstructs a 128×128-pixel image by filling data for the phase encoding direction by calculation according to the half Fourier method.

Figure 3B:
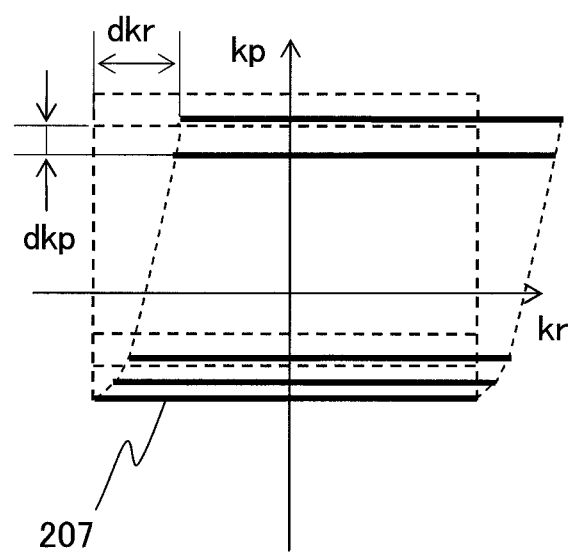
FIG. 3B is a drawing for explaining the k-space according to DWEPI used in an embodiment of the present invention.

As described above, when a DWEPI sequence is executed, a temporally changing magnetic field error is generated due to eddy currents and vibrations associated with application of MPG pulse. Since the spatial main components of the magnetic field error are linear components, the magnetic field error causes distortion of k-space data as shown in FIG. 3B. Therefore, if a usual image reconstruction processing is performed with such k-space data as they are, artifacts (distortion and blurring) will occur in the image obtained.

Therefore, in this embodiment, reference data is obtained by the reference data acquisition part performing a reference measurement in advance of main scan, and characteristic data of the magnetic field error serving as a factor of generating distortion in the k-space data are calculated from the reference data by the characteristic data calculation part. Then, main scan is performed, and distortion of the k-space data obtained in the main scan is eliminated by the correction processing part using the characteristic data. The characteristic data referred to here are provided with distortion amounts of the k-space data per unit gradient magnetic field strength of the MPG pulse (distortion amount in the read-out direction: dkr, distortion amount in the phase encoding direction: dkp) and phase offset amounts ($p_o$). The details of the processing operations performed by those parts will be explained below.

First, the reference data acquisition processing performed by the reference data acquisition part will be explained. In the reference data acquisition processing, the same DWEPI sequence as that used in main scan is executed by using basically the same imaging parameters as those used in the main scan as a reference measurement to obtain reference data for calculating characteristic data. Generally, a magnetic field error induced by vibration or eddy current is not spatially uniform, and the characteristic data depend on direction and position of slice. Therefore, characteristic data for a plurality of slice positions are required for every slice direction. In order to correct k-space data obtained by main scan, characteristic data for at least the same slice direction as the slice direction of the main scan are required. This embodiment will be explained with reference to an example where, the reference measurement is performed for a plurality of slice positions with setting the slice direction to the same direction as the slice direction of the main scan, and characteristic data for the same direction as the slice direction of main scan are calculated from the obtained reference data. In the following explanations, the slice direction in the main scan is the z-direction, for example.

Figure 4A:
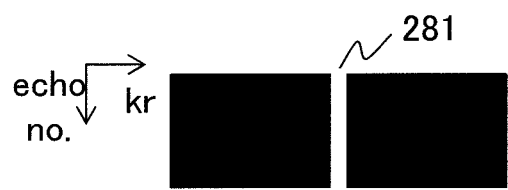
FIG. 4A shows an example of reference data obtained without applying MPG pulse in an embodiment of the present invention.
Figure 4B:
FIG. 4B shows an example of reference data obtained with applying MPG pulse in an embodiment of the present invention.

Among the characteristic data, the distortion amount for the read-out direction dkr can be observed as change in peak position (peak shift) between echoes obtained with and without applying the MPG pulse, among echoes measured with the DWEPI sequence shown in FIG. 2A where strengths of all the gradient magnetic field pulses (204 and 210) in the phase encoding direction are zero. Examples of the first reference data obtained with the DWEPI sequence where strengths of all the gradient magnetic field pulses in the phase encoding direction are zero are shown in FIG. 4A and FIG. 4B. FIG. 4A shows an example obtained without applying a MPG pulse, and FIG. 4B shows an example obtained by applying a MPG pulse in one direction along one of the x, y and z-axes. As shown in these drawings, when the MPG pulse is not applied, an echo peak position 281 (portion showing high intensity) locates at the center (original) for the read-out direction (kr direction) regardless of the echo number. However, when the MPG pulse 211 is applied, an echo peak position 281' of a later echo shifts more in the read-out direction (kr direction). As described above, the distortion of the k-space data due to eddy currents generated by the MPG pulse 211 appears as a shift of the echo peak position 281. Therefore, distortion of k-space data can be measured by detecting amount of shift of the echo peak position 281' obtained with applying the MPG pulse 211 from the echo peak position 281 obtained without applying the MPG pulse.

In this embodiment, the distortion amounts of k-space data in the read-out direction dkr are calculated from the amounts of peak shift between echoes obtained with and without applying an MPG pulse in the first reference data obtained as described above. The peak shift amounts of echoes are equal to the first order components of the phases of projection data obtained by inverse Fourier transform of the echoes according to the principle of the Fourier transform. That is, if the peak position shifts by one sampling point in the kr direction, phase difference between sampling points of the both ends of the projection data will change by 2π. Therefore, the distortion amounts of k-space data in the read-out direction dkr are obtained as first order components of the phase differences between the projection data obtained by inverse Fourier transform in the read-out direction of the first reference data obtained by applying the MPG pulse, and the projection data obtained from the first reference data without application of the MPG pulse. Further, distortion amounts in the phase encoding direction dkp are similarly calculated from the second reference data measured by interchanging the read-out direction and the phase encoding direction used for obtaining the first reference data. Further, the phase offset amount $p_0$ is a difference of peak phase between echoes of the reference data obtained with and without applying the first MPG pulse. The phases of echo peaks are equal to the zero-order components of the phases of the projection data obtained by inverse Fourier transform of the echoes according to the principle of the Fourier transform. Therefore, the phase offset amounts $p_0$ are obtained as zero-order components of the phase differences between the projections obtained with and without applying the MPG pulse in the first reference data.

On the basis of the above, the reference data acquisition part executes four kinds of sequences of applying the MPG pulse along the x, y and z-axis and not applying the MPG pulse, in which pulse strengths of all the phase encoding gradient magnetic field pulses are 0, for the first sets of the read-out direction and the phase encoding direction at a plurality of slice positions as a reference measurement to obtain first reference data. Similarly, four kinds of the sequences are executed at a plurality of the same slice positions with interchanging the read-out direction and the phase encoding direction to obtain second reference data. The pulse sequences to be executed are fundamentally the same as the DWEPI sequence shown in FIG. 2A except for the aforementioned conditions.

In this example, since the slice direction of main scan is defined to be the z-direction, the measurement parameters of the reference measurement in which the aforementioned 8 kinds (8 sets) of multi-slice imaging are performed can be, for example, as follows.

Slice direction: z-direction
Read-out direction and phase encoding direction: two types of combinations, the x-direction and the y-direction (henceforth referred to as AP), and the y-direction and the x-direction (henceforth referred to as RL)
MPG pulse: Four types of those applied in the x-axis direction, y-axis direction and z-axis direction, and no application
Phase encoding gradient magnetic field pulse strength: 0
Number of slices: 20
Slice spacing: 1 cm
Echo interval (IET): 1 ms
Number of multi-echo: 100

The values of the measurement parameters other than the measurement parameters to be varied (variable parameters: combination of read-out direction and phase encoding direction, presence or absence of application of MPG pulse, axis for MPG pulse application) should be the same in 8 sets of the reference measurements. Further, the values of the measurement parameters other than the measurement parameters to be varied and the phase encoding gradient magnetic field pulse strength are desirably the same as those defined as imaging conditions of main scan. In particular, since the characteristic data calculated from the reference data depend on the slice direction or ON/OFF time of the MPG pulse, the slice direction, application time and application interval of the MPG pulse are made closer to those defined as the imaging parameters of main scan as much as possible. Further, the strength of the MPG pulse used in the reference measurement is tuned so that peak position can be detected up to the last echo. In general, degree of magnetic field error is proportional to the MPG pulse strength. Therefore, if a strength of the MPG pulse equivalent to that used in the main scan is used in the reference measurement, strength may be too large, thus echoes may decayed by the magnetic field error in an short period of time, and the peak position may not be detected up to the last echo. Therefore, the MPG pulse strength used in the reference measurement is often set to be smaller than the pulse strength used in the main scan.

Hereafter, the characteristic data calculation processing performed by the characteristic data calculation part will be explained. By using the reference data $s_0$ obtained by the reference data acquisition part through 8 sets of the reference imaging, the characteristic data calculation part calculates distortion amounts of k-space data (dkr, dkp) and the phase offset amounts $p_0$ as functions of center time of echo and slice position at the time of obtaining the reference data.

That is, the characteristic data calculation part calculates distortion amounts in the read-out direction $dkr_m$, distortion amounts in the phase encoding direction $dkp_m$, and phase offset amounts $p_{0m}$ for every MPG pulse application axis m (m is x, y or z) according to the equations of the following equation group (1). The values contained in the equations of the equation group (1) are normalized with the MPG pulse strength and field of view.

$$\left. \begin{array}{l} dkr'_m(t', z') = F_{1,1}\left[\text{Arg}\left[\dfrac{FT^{-1}[s_{0,AP,m,b_1}(t', z')]}{FT^{-1}[s_{0,AP,b_0}(t', z')]}\right]\right] n_r/(2\pi w_{r0}b_1) \\[6pt] dkp'_m(t', z') = F_{1,1}\left[\text{Arg}\left[\dfrac{FT^{-1}[s_{0,RL,m,b_1}(t', z')]}{FT^{-1}[s_{0,RL,b_0}(t', z')]}\right]\right] n_p/(2\pi w_{p0}b_1) \\[6pt] p'_{0m}(t', z') = F_{1,0}\left[\text{Arg}\left[\dfrac{FT^{-1}[s_{0,AP,m,b_1}(t', z')]}{FT^{-1}[s_{0,AP,b_0}(t', z')]}\right]\right]/b_1 \\[6pt] dkr_m(t', z') = dkr'_m(t', z') - dkr'_m(T'_{00}, z) \\ dkp_m(t', z') = dkp'_m(t', z') - dkp'_m(T'_{00}, z) \\ p'_{0m}(t', z') = p'_{0m}(t', z') - p'_{0m}(T'_{00}, z) \\ m = \{x, y, z\} \\ t' = T_{00} + (i-1)T_{e0}, i = \{1, \ldots, n_{e0}\} \\ z' = S_{0j}, j = \{1, \ldots, n_{s0}\} \end{array} \right\} \quad (1)$$

In the equations of the equation group (1), reference data (echo) $s_{0*}$ means reference data (echoes) measured in 8 sets of the aforementioned reference measurement under the conditions indicated at the position of the subscript * (read-out direction, phase encoding direction, and MPG pulse application axis). AP and RL represents the set of the read-out direction and the phase encoding direction, $m, b_1$ means that the MPG pulse is applied in the m axis direction, and $b_0$ means that the MPG pulse was not applied. In addition, $b_1$ also represents pulse strength of the MPG pulse. Further, t' represents center time of each echo in the reference measurement, $n_{e0}$ represents echo number in the reference measurement, $T_{e0}$ represents echo interval in the reference measurement, $T_{00}$ represents time from the off time of the last MPG pulse to the center time of the first echo in the reference measurement, z' ($=S_{0j}$) represents slice position in the reference measurement, $n_{s0}$ represents slice number in the reference measurement, $FT^{-1}[*]$ represents inverse Fourier transform, $\text{Arg}[*]$ represents a function providing a phase for each sampling point of a variable *, $F_{1,1}[*]$ and $F_{1,0}[*]$ represent functions providing coefficient of first order term and absolute term of a linear function obtained by linear function fitting of data for only a "region including signals", respectively, $w_{r0}$ and $w_{p0}$ represent fields of view in the read-out direction of AP and RL, respectively, and $n_r$ and $n_p$ represents numbers of sampling points of AP and RL in the read-out direction, respectively. In addition, the definition ranges for the fitting (coordinate range of sampling points) are $[-n_r/2, n_r/2-1]$ and $[-n_p/2, n_p/2-1]$ for AP and RL, respectively.

The "region including signals" is, for example, a region of a pixel showing a intensity value not smaller than a predetermined value in a projection of echoes measured first (first echoes). Specifically, for example, a value obtained by multiplying the maximum intensity value of projection of the first echoes with 0.7 is set as a threshold value, and a region including a pixel showing a intensity value not smaller than the threshold value is defined as the "region including signals". Such a region is defined as "region including signals" for all the echoes obtained thereafter. The coefficient for obtaining the threshold value (0.7) varies depending on such conditions as S/N ratio of the data.

The characteristic data calculation processing for calculating characteristic data carried out by the characteristic data calculation part using the equations of the equation group (1) will be explained below. FIG. 5A and FIG. 5B are drawings for explaining the flow of the characteristic data calculation processing according to this embodiment for AP and RL, respectively. The following processing is executed for every MPG pulse application axis m = {x, y, z}. In this explanation, the axis is generically indicated with m. As shown in this drawing, the characteristic data calculation part performs one-dimensional inverse Fourier transform of the reference data (501, 503) obtained with the sequence including application of the MPG pulse along the m-axis and the reference data (502, 504) obtained without application of the MPG pulse for each of AP and RL (steps 505, 506, 507 and 508) to obtain projection data. For each of AP and RL, the projection data calculated from the reference data obtained with applying the MPG pulse are divided with the projection data calculated from the reference data obtained without applying the MPG pulse (steps 509 and 510). Since this processing is division of complex data, it is equivalent to obtaining difference of phases of projections. Phase values are calculated from the respective results (complex data) (steps 511 and 512), and fitted with a linear function. As for AP, coefficient of the first order term and the absolute term of the linear function are calculated, and as for RL, coefficient of the first order term is calculated (steps 513, 514, 515). For these results, normalization is performed by using the pulse strength of the MPG pulse and the field of view (516, 517, 518) of the read-out direction to obtain characteristic data (522, 523, 524) (steps 519, 520 and 521).

The correction processing carried out by the correction processing part for the k-space data obtained by main scan using the characteristic data (dkr, dkp, $P_0$) represented by the equations of the equation group (1), which are calculated by the characteristic data calculation part through the procedure described above. The main scan is performed by the diffusion-weighted measurement part using a DWEPI sequence. Explanation will be made here for an example of imaging where the slice direction is the z-direction as mentioned above, the read-out direction is the x-direction, and the phase encoding direction is the y-direction. The obtained imaging data s'* is represented as shown in (2) mentioned below as a function of the center time t and the slice position z of each echo at the time of the main scan.

$$s'_{AP,g_x,g_y,g_z}(t,z) \quad (2)$$

wherein $$t = T_0 + (i-1)T_e, i = \{1, \ldots, n_e\}$$

$$z = S_j, j = \{1, \ldots, n_s\}$$

and s'* means imaging data obtained with conditions indicated at the position of the subscript * in the main scan. Here, $g_x$, $g_y$ and $g_z$ represent strengths of the MPG pulse for the corresponding axes at the time of the main scan, $n_e$ represents number of echoes at the time of the main scan, $T_e$ represents echo interval at the time of the main scan, $T_0$ represents time from the OFF time of the last MPG pulse to the center time of the first echo at the time of the main scan, $S_j$ (=z) represents slice position at the time of the main scan, and $n_s$ represents slice number at the time of main scan.

The correction processing part performs phase offset correction first by using the phase offset amounts $p_0$. The phase offset correction amounts of the imaging data s'* are calculated by proportional addition of the MPG pulse strengths $g_m$ of the characteristic data $p_{0m}$ for every MPG pulse application axis. Therefore, imaging data s''* after the phase offset correction can be obtained according to the following equation (3).

$$s''_{AP,g_x,g_y,g_z}(t,z) = s'_{AP,g_x,g_y,g_z}(t,z) \mathrm{Exp}[I(g_x p_{0_x}(t,z) + g_y p_{0_y}(t,z) + g_z p_{0_z}(t,z))] \quad (3)$$

In the equation, I represents an imaginary unit.

Following the phase offset correction, k-space data distortion correction for correcting distortion of k-space data is performed by using the distortion amounts for the read-out direction dkr and the distortion amounts for the phase encoding direction dkp. In the k-space data distortion correction, on the basis of the relationship of the actual positions (kr', kp') of echoes of the imaging data s''* in the k-space and sampling points distributed in a grid pattern (kr, kp) represented by the equations of the following equation group (4), signal values of the sampling points distributed in a grid pattern (kr, kp) are calculated by gridding.

$$\left. \begin{array}{l} kr' = kr - (g_x dkr_x(t,z) + g_y dkr_y(t,z) + g_z dkr_z(t,z))w_r \\ kp' = kp - (g_x dkp_x(t,z) + g_y dkp_y(t,z) + g_z dkp_z(t,z))w_p \end{array} \right\} \quad (4)$$

In the equations, $w_r$ and $w_p$ represent fields of view for the read-out direction and the phase encoding direction in main scan, respectively.

In addition, when the center time t' and slice position y' of each echo at the time of the reference imaging are different from those in the main scan, t and y, $P_{0m}(t,z)$, $dkr_m(t,z)$ and $dkp_m(t,z)$ in the aforementioned equation (3) and the equations of the equation group (4) are obtained by linear interpolation of $p_{0m}(t',z')$ $dkr_m(t',z')$ and $dkp_m(t',z')$ in the directions of t' and z'.

Figure 6:
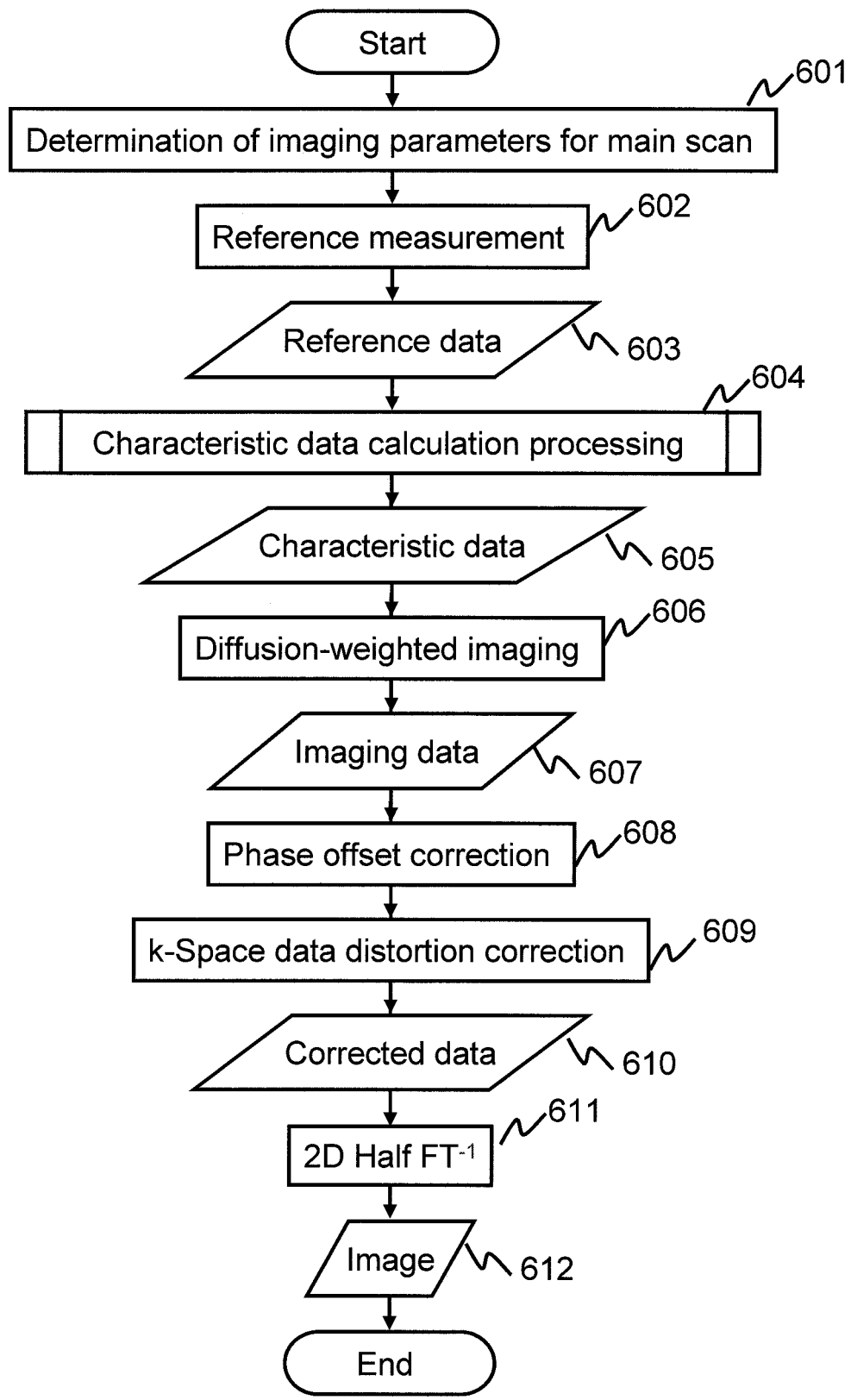
FIG. 6 shows a process flowchart of imaging according to an embodiment of the present invention.

Flow of the processing performed by the processing parts in the diffusion-weighted imaging according to this embodiment will be explained below. Explanation will be made here with an assumption that, when imaging parameters of main scan are determined, characteristic data are obtained for the slice direction in the main scan. FIG. 6 shows a process flow of imaging according to this embodiment. When imaging parameters of main scan are determined (step 601), the reference data acquisition part performs reference measurement with the same slice direction as that of the main scan (step 602) to obtain reference data (603). The characteristic data calculation part performs the characteristic data calculation processing by using the reference data (step 604) to calculate characteristic data (605).

The diffusion-weighted measurement part performs the diffusion-weighted imaging (step 606) by using the imaging parameters determined in the step 601 to obtain imaging data (607). The correction processing part performs the phase offset correction (step 608) for the imaging data by using the phase offset amounts $p_0$ included in the characteristic data. Then, the correction processing part performs the k-space data distortion amount correction for the data after the phase offset correction processing by gridding using the of k-space data distortion amounts (dkr, dkp) (step 609) to obtain corrected data (610). The image reconstruction part performs two-dimensional inverse half-Fourier transform (2D half $FT^{-1}$, step 611) of the k-space data after the k-space data distortion amount correction to obtain an image (612).

Figure 7A:
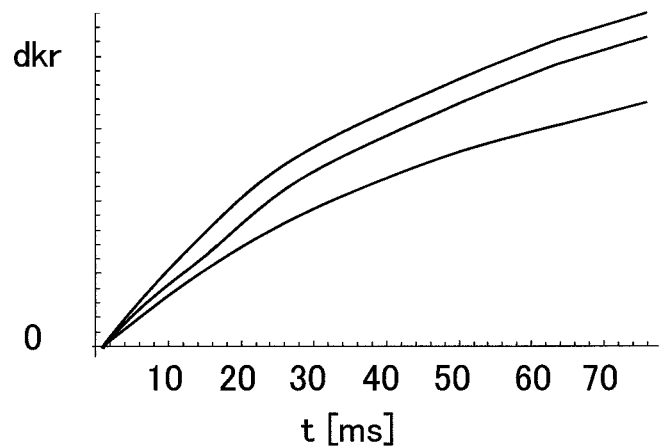
FIG. 7A is a graph showing characteristic data of dkr obtained in an embodiment of the present invention.
Figure 7B:
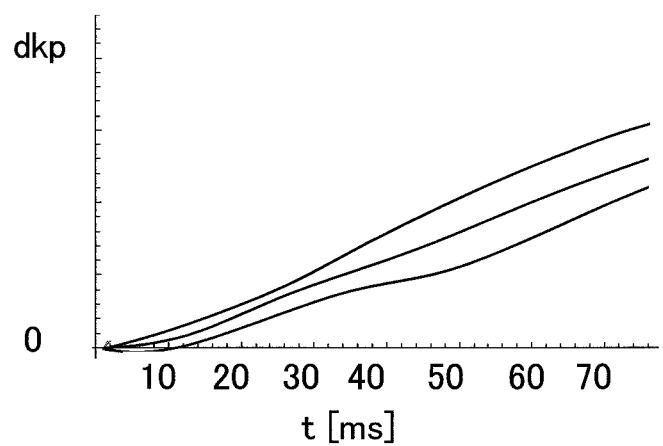
FIG. 7B is a graph showing characteristic data of dkp obtained in an embodiment of the present invention.
Figure 7C:
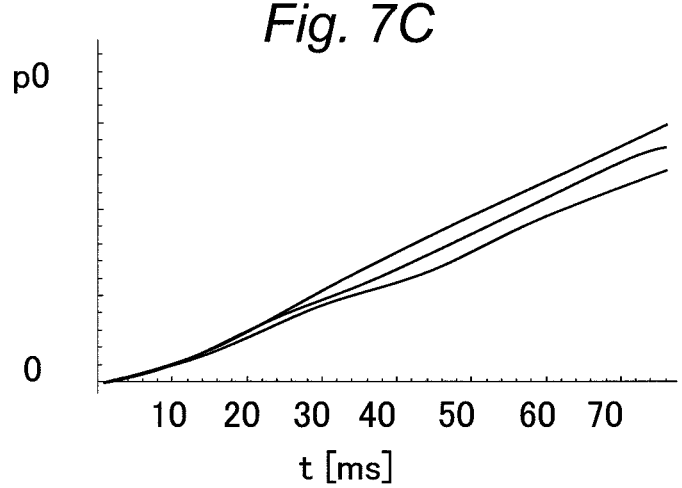
FIG. 7C a graph showing characteristic data of $p_o$ obtained in an embodiment of the present invention.

Examples of the k-space data distortion amounts (dkr, dkp) and the phase offset amounts $p_0$ calculated by the characteristic data calculation part according to the procedure of the aforementioned embodiment are shown in FIG. 7A, FIG. 7B, and FIG. 7C. The graphs show the values of 3 slices among the 20 slices described above. As shown in these graphs, the characteristic data of the slices are significantly different from one another. Since the aforementioned characteristic data are calculated by measuring reference data for every slice in this embodiment, correction with optimal correction values becomes possible for every slice, i.e., every position in the slice direction.

Figure 8A:
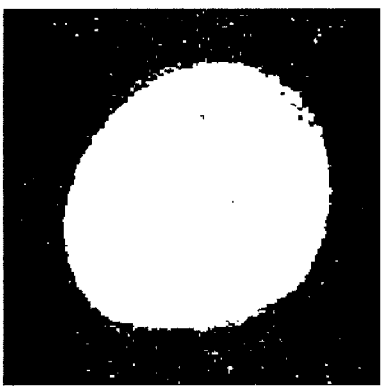
FIG. 8A is a drawing for explaining effect of correction according to an embodiment of the present invention (image before correction).
Figure 8B:
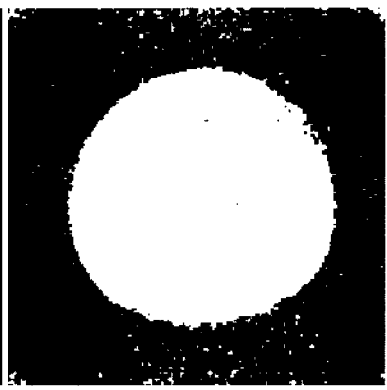
FIG. 8B is a drawing for explaining effect of correction according to an embodiment of the present invention (image after correction).
Figure 8C:
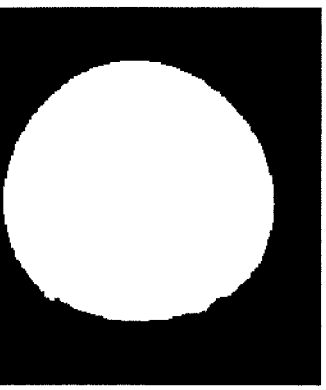
FIG. 8C is a drawing for explaining effect of correction according to an embodiment of the present invention (image obtained without applying MPG pulse).

Further, examples of images including one obtained by the correction according to the procedure described above are shown in FIG. 8A, FIG. 8B and FIG. 8C. FIG. 8A, FIG. 8B and FIG. 8C show images for one slice among 20 slices obtained by performing multi-slice imaging. FIG. 8A shows an image obtained before the correction, FIG. 8B shows an image obtained after the correction, and FIG. 8C shows an image obtained with an MPG pulse of which strength is zero, and image contrast is enhanced in these images so as to clarify the effect of the correction. It can be seen that distortion and blurring are more generated by the MPG pulse in the image shown in FIG. 8A compared with the image shown in FIG. 8C. In contrast, as shown in FIG. 8B, it can be seen that by performing the correction processing of this embodiment, distortion and blurring are suppressed and an image equivalent to the image shown in FIG. 8C can be obtained. The larger noise in the image of FIG. 8, B was provided by the effect of the diffusion-weighting.

As explained above, according to this embodiment, the k-space data distortion amounts in a slice in the read-out direction and in the phase encoding direction and the phase offset amounts induced by a diffusion-weighted gradient magnetic field pulse are calculated as characteristic data for every slice position, and the k-space data obtained by main scan are corrected by using the characteristic data. Therefore, highly precise correction values can be obtained for every slice. Accordingly, accuracy of the correction is also increased, and image quality of the images obtained by the diffusion-weighted imaging is improved. That is, according to this embodiment, there can be provided a magnetic resonance imaging device with which the influence of magnetic field error resulting from eddy currents and vibrations induced by a diffusion-weighted gradient magnetic field pulse can be corrected with good precision, and blurring and distortion in diffusion-weighted images can be suppressed.

FIG. 9A and FIG. 9B show results obtained by correcting data of imaging obtained under the same conditions according to a conventional method, and according to the procedure of this embodiment. FIG. 9A shows results obtained by correction according to a conventional method, i.e., correction in which all the slices were corrected with the same correction values, and FIG. 9B shows results obtained by correction according to the procedure of this embodiment, i.e., correction performed with correction values specific to each slice. In these images, circles are indicated at positions of original outlines of a subject to emphasize the difference of the effect, and the lower images are shown with enhanced image contract. It can be confirmed that the blurring seen around the upper pert of the circular phantom in the image of FIG. 9A was suppressed in the image of FIG. 9B, and an image uniform as a whole could be obtained.

The characteristic data must be calculated for every slice direction. Therefore, the aforementioned embodiment was explained with reference to an example where the reference measurement providing the basis of the calculation of the characteristic data is performed for the same slice direction as the slice direction of the main scan (for example, z-direction) to calculate minimum characteristic data required, and the correction is performed with them. However, calculation scheme of the characteristic data is not limited to such a procedure as mentioned above.

The magnetic field error depends on the device (magnet and gradient coil), and does not depend on an object of imaging. That is, since characteristic data of an device are data specific to the device, if they are measured once, they can be commonly used in imaging operations thereafter. Therefore, in order to shorten the imaging time, it may be configured that data for all the slice directions required for the subsequent main scan are obtained beforehand, and stored in a storage medium 111. In such a case, in the process flow shown in FIG. 6 mentioned above, the steps 602 and 604 are repeated for each slice direction to obtain characteristic data for all the directions.

Further, the aforementioned embodiment was explained for an example where the slice direction, the read-out direction, and the phase encoding direction used in the reference measurement are the same as those used in the main scan. However, selection of these directions is not limited to such selection as mentioned above. For example, the read-out direction and the phase encoding direction may be opposite to each other. Further, the directions of the axes may deviate from each other, so long as the deviation is within a predetermined range (about 20 to 30 degrees).

Further, the aforementioned embodiment was explained for an example where the slice position z' and the echo peak time t' defined in the reference measurement are not necessarily the same as the slice position z and the echo peak time t defined in the main scan. However, the imaging parameters of the reference imaging may be set so as to be the same as those of the main scan. In this case, the linear interpolation performed for the equation groups (3) and (4) mentioned above is unnecessary, and thus precision of the correction is increased.

In the aforementioned embodiment, the reference data are obtained with changing m among three kinds of directions of x, y and z, and the characteristic data are calculated so that the correction can be performed regardless of the application direction of the MPG pulse in the main scan. However, it is not necessarily required to obtain reference data and perform calculation of characteristic data for three of the x, y and z-axes. It may be configured that the reference measurement is performed by applying an MPG pulse only in the same direction as the MPG pulse application direction of the main scan. For example, when application strengths of the MPG pulse for the axes in the main scan are ($g_x$, $g_y$, $g_z$), and the application direction is $m_I$ ($m_I$=($g_x$, $g_y$, $g_z$)/|($g_x$, $g_y$, $g_z$)|) $m_I$ is used as the MPG pulse application direction in the reference measurement, and the pulse strength thereof is defied as ($g_x'$, $g_y'$, $g_I'$), and characteristic data are calculated with m=$m_I$ and $b_1$=$\sqrt{(g_x'^2+g_y'^2+g_z'^2)}$ instead of performing calculation of the equations of the equation group (1) for the three kinds of m={x, y, z}. The correction can be thereby attained as in the case of the aforementioned embodiment. Further, since the same MPG pulse direction can be used in the reference measurement and the main scan, precision of the correction can be more improved. Furthermore, the number of reference measurement can be reduced to shorten the measurement time. When not more than 2 of MPG pulse application directions are used in the main scan, in particular, the number of times of the reference measurement can be reduced, and therefore the measurement time can be shortened. In addition, also in this case, if the imaging parameters of the reference measurement are chosen so that the slice position z' and the echo peak time t' in the reference measurement are the same as the slice position z and the echo peak time t in the main scan, linear interpolation becomes unnecessary, and precision of the correction is improved. Further, in this case, the slice number of the reference measurement may also be the same as that of the main scan. For example, when the slice number is 1 in the main scan, the slice number may also be 1 in the reference measurement.

Further, odd-numbered values and even-numbered values of the k-space data distortion amounts (dkr, dkp) and the phase offset amounts $p_0$ calculated by the procedure explained for the aforementioned embodiment may be systematically slightly different from each other. In such a case, averages of temporally adjacent values can be calculated according to the equations of the following equation group (5) to improve precision of the correction.

$$dkr_m(t', z') = \text{Mean}[dkr_m(t', z') + dkr_m(t' + T_{e0}, z')]$$
$$dkp_m(t', z') = \text{Mean}[dkp_m(t', z') + dkp_m(t' + T_{e0}, z')] \quad (5)$$
$$p_{0m}(t', z') = \text{Mean}[p_{0m}(t', z') + p_{0m}(t + T_{e0}, z')]$$

Further, although the correction is performed for the influence of magnetic field error induced by a diffusion-weighted gradient magnetic field pulse in the explanation of the aforementioned embodiment, the object of the correction is not limited to such an object. The correction can also be performed for other considerable influences of a magnetic field error induced by a gradient magnetic field pulse that generates eddy currents and vibrations.

Denotation of Reference Numerals

101: Magnet generating static magnetic field, 102: gradient coil, 103: subject, 104: sequencer, 105: gradient magnetic field power supply, 106: radio frequency magnetic field generator, 107: probe, 108: receiver, 109: computer, 110: display, 111: storage medium

The invention claimed is:

1. A magnetic resonance imaging device comprising at least one of a hardware processor and circuitry effecting:
   an imaging portion configured to apply a radio frequency magnetic field and a gradient magnetic field to a subject placed in a static magnetic field and to detect magnetic resonance signals generated from the subject, a calculator configured to process the magnetic resonance signals detected by the imaging portion, and a controller configured to control the imaging portion and the calculator, wherein:
   the imaging portion including:
   a diffusion-weighted imaging execution portion configured to detect the magnetic resonance signals according to a pulse sequence including a diffusion-weighted gradient magnetic field pulse, and
   a reference data acquisition portion configured to obtain reference data for detecting distortion amounts of k-space data caused by the diffusion-weighted gradient magnetic field pulse at an arbitrary position in a slice direction, and the calculator including:
a characteristic data calculation portion configured to calculate distortion amounts for a read-out direction and a phase encoding direction and phase offset amounts at an arbitrary position in the slice direction from the reference data as characteristic data of the amounts of distortion of k-space data,
a correction portion configured to correct the k-space data constituted by the magnetic resonance signals acquired by the diffusion-weighted imaging execution portion by using the characteristic data, and
an image reconstruction portion configured to reconstruct an image from the data corrected by the correction portion.

2. The magnetic resonance imaging device according to claim 1, wherein:
the reference data acquisition portion is configured to obtain the reference data by executing:
a sequence corresponding to the pulse sequence executed by the diffusion-weighted imaging execution portion in which pulse strength of a phase encoding gradient magnetic field pulse is 0, and the diffusion-weighted gradient magnetic field pulse is applied,
a sequence corresponding to the pulse sequence in which pulse strength of a phase encoding gradient magnetic field pulse is 0, and the diffusion-weighted gradient magnetic field pulse is not applied along any of axes,
a sequence corresponding to the pulse sequence in which the read-out direction and the phase encoding direction of the pulse sequence are interchanged, pulse strength of a phase encoding gradient magnetic field pulse is 0, and the diffusion-weighted gradient magnetic field pulse is applied, and
a sequence corresponding to the pulse sequence in which the read-out direction and the phase encoding direction of the pulse sequence are interchanged, pulse strength of a phase encoding gradient magnetic field pulse is 0, and the diffusion-weighted gradient magnetic field pulse is not applied along any of axes.

3. The magnetic resonance imaging device according to claim 2, wherein:
the characteristic data calculation portion is configured to:
calculate the amounts of distortion in the read-out direction and the phase offset amounts of the k-space data by using shift amounts in the read-out direction of reference data obtained with a sequence corresponding to the pulse sequence in which the read-out direction and the phase encoding direction are the same as those of the pulse sequence, and the diffusion-weighted gradient magnetic field pulse is applied, from reference data obtained with a sequence corresponding to the pulse sequence in which the read-out direction and the phase encoding direction are the same as those of the pulse sequence, and the diffusion-weighted gradient magnetic field pulse is not applied, and
calculate the amounts of distortion in the phase encoding direction of the k-space data by using shift amounts in the read-out direction of reference data obtained with a sequence corresponding to the pulse sequence in which the read-out direction and the phase encoding direction of the pulse sequence are interchanged, and the diffusion-weighted gradient magnetic field pulse is applied, from reference data obtained with a sequence corresponding to the pulse sequence in which the read-out direction and the phase encoding direction of the pulse sequence are interchanged, and the diffusion-weighted gradient magnetic field pulse is not applied.

4. The magnetic resonance imaging device according to claim 3, wherein:
the characteristic data calculation portion is configured to:
calculate the shift amounts in the read-out direction of the distortion amounts in the read-out direction and the distortion amounts in the phase encoding direction of the k-space data as first order components of phase differences between projection data obtained by inverse Fourier transform in the read-out direction of the reference data obtained by applying the diffusion-weighted gradient magnetic field pulse and projection data obtained by inverse Fourier transform in the read-out direction of the reference data obtained without applying the diffusion-weighted gradient magnetic field pulse, and
calculate the shift amounts of the phase offset amounts as zero order components of phase differences between projection data obtained by inverse Fourier transform in the read-out direction of the reference data obtained by applying the diffusion-weighted gradient magnetic field pulse and projection data obtained by inverse Fourier transform in the read-out direction of the reference data obtained without applying the diffusion-weighted gradient magnetic field pulse.

5. The magnetic resonance imaging device according to claim 1, wherein:
there are a plurality of slice positions, and
the correction portion is configured to perform the correction by calculating the phase offset amounts and the amounts of distortion in the read-out direction and the phase encoding direction of k-space data to be corrected at a slice position from characteristic data for each of a plurality of the slice positions for which the reference data are obtained.

6. The magnetic resonance imaging device according to claim 5, wherein:
the phase offset amounts and the amounts of distortion in the read-out direction and the phase encoding direction of k-space data to be corrected at a slice position are calculated by linear interpolation in the slice direction of the characteristic data for each of a plurality of the slice positions for which the reference data are obtained.

7. The magnetic resonance imaging device according to claim 1, wherein:
the correction portion is configured to perform phase offset correction of the k-space data by using the phase offset amounts, and to perform correction of the k-space data after the phase offset correction by gridding using the amounts of distortion in the read-out direction and the phase encoding direction calculated by the characteristic data calculation unit.

8. The magnetic resonance imaging device according to claim 1, wherein:
the read-out direction at the time of obtaining the reference data is substantially the same as either one of the read-out direction and the phase encoding direction of the pulse sequence executed by the diffusion-weighted imaging execution portion.

9. The magnetic resonance imaging device according to claim 1, wherein:
strength of the diffusion-weighted gradient magnetic field pulse applied at the time of obtaining the reference data is smaller than strength of the diffusion-weighted gradient magnetic field pulse applied by the pulse sequence executed by the diffusion-weighted imaging execution portion.

10. The magnetic resonance imaging device according to claim 2, wherein:

imaging parameters of the pulse sequence executed by the reference data acquisition portion for obtaining the reference data are the same as imaging parameters of the pulse sequence executed by the diffusion-weighted imaging execution portion except for strength of the phase encoding gradient magnetic field pulse and strength of the diffusion-weighted gradient magnetic field pulse.

11. The magnetic resonance imaging device according to claim 1, wherein:
the characteristic data calculation portion is configured to normalize the characteristic data with fields of view in the read-out direction and the phase encoding direction of the pulse sequence executed by the reference data acquisition portion for obtaining the reference data and applied strength of the diffusion-weighted gradient magnetic field pulse.

12. The magnetic resonance imaging device according to claim 2, wherein:
the sequence for applying the diffusion-weighted gradient magnetic field pulse applies the diffusion-weighted gradient magnetic field pulse along each of the x, y and z-axes.

13. The magnetic resonance imaging device according to claim 1, wherein:
the reference data acquisition portion is configured to obtain the reference data by executing a sequence applying the diffusion-weighted gradient magnetic field pulse and a sequence not applying the diffusion-weighted gradient magnetic field pulse.

* * * * *